(12) United States Patent
Diehl et al.

(10) Patent No.: US 6,359,009 B1
(45) Date of Patent: Mar. 19, 2002

(54) SUBSTITUTED ANILIDE INSECTICIDAL AGENTS

(75) Inventors: Robert Eugene Diehl, Yardley, PA (US); Tatao Luo, Moraga, CA (US); Michael Frank Treacy; Keith Douglas Barnes, both of Newton, PA (US); Venkataraman Kameswaran, Trenton, NJ (US)

(73) Assignee: BASF Aktiengesellschaft, NC (US)

( * ) Notice: Subject to any disclaimer, the term of this patent is extended or adjusted under 35 U.S.C. 154(b) by 0 days.

(21) Appl. No.: 09/277,656

(22) Filed: Mar. 26, 1999

Related U.S. Application Data

(60) Provisional application No. 60/081,072, filed on Apr. 8, 1998.

(51) Int. Cl.$^7$ ................ A01N 37/18; A61K 21/165
(52) U.S. Cl. ................ 514/621; 514/617; 514/625; 564/161; 564/218
(58) Field of Search ................ 564/161, 218; 514/617, 621, 625

(56) References Cited

U.S. PATENT DOCUMENTS 3,072,724 A    1/1963   Elam et al. ............ 260/561

FOREIGN PATENT DOCUMENTS

CH          148911        6/1973

OTHER PUBLICATIONS

Abstract to Luo et al., "Synthesis of 2–(+/–)–(4–iodobenzyloxy)propanoic acid and its derivatives", Yanbian Daxue Xuebao, Ziran Kexueban 24(3), pp. 22–24, 1998.*
Abstract to Sato et al., "Synthesis of beta–ketocarboxamide derivatives using 2,2–dimethyl–2H, 4H–1, 3–dioxin–4–ones", Chem. Pharm. Bull., 32(10), pp. 3848–3856, 1984.*
Journal of Organic Chemistry, 26, pp. 4340–4344 (1961).
Journal of Organic Chemistry, 27, pp. 60–64 (1962).
Chemical Abstracts: 79 136775v (1973).
Collect. Czech. Chem. Commun., 36(5), pp. 1995–2004 (1971).

\* cited by examiner

*Primary Examiner*—Dwayne C. Jones

(57) ABSTRACT

Pesticidal substituted anilide compounds having the structural formula I

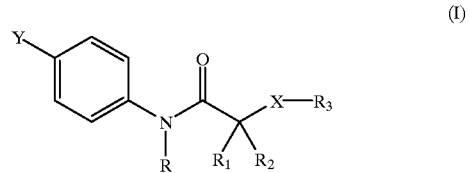

and compositions and methods comprising those compounds for the control of insect pests.

25 Claims, No Drawings

SUBSTITUTED ANILIDE INSECTICIDAL AGENTS

This application claims priority to Provisional Application No. 60/081,072, filed on Apr. 8, 1998.

BACKGROUND OF THE INVENTION

Insect pests destroy growing and harvested crops. In the United States, agronomic crops must compete with thousands of those pests. In particular, soil-dwelling Coleoptera such as southern corn rootworm, northern corn rootworm, western corn rootworm and Mexican corn rootworm are especially devastating to crops such as corn.

In spite of the commercial insecticides available today, damage to crops, both growing and harvested, caused by insect pests still occurs. Accordingly, there is ongoing research to create new and more effective insecticidal agents.

Certain N-substituted-2,2,4-trimethyl-3-oxovaleramide compounds are described in Czech. patent number 148,911; Collect. Czech. Chem. Commun., 36(5), pp. 1995–2004 (1971); Journal of Organic Chemistry, 26, pp. 4340–4344 (1961); Journal of Organic Chemistry, 27, pp. 60–64 (1962); and U.S. Pat. No. 3,072,724. However, no insecticidal utility is described for those compounds.

It is, therefore, an object of the present invention to provide compounds which are effective for the control of insect pests.

It is also an object of the present invention to provide a method for the control of insect pests.

It is a further object of this invention to provide a method for the protection of growing and harvested crops from damage caused by insect attack and infestation.

These and other objects of the present invention will become more apparent from the detailed description thereof set forth below.

SUMMARY OF THE INVENTION

The present invention comprises substituted anilide compounds which are useful as insecticidal agents. Those compounds are also useful for protecting plants from damage caused by insect attack and infestation.

The insecticidal substituted anilide compounds of the present invention have the structural formula I

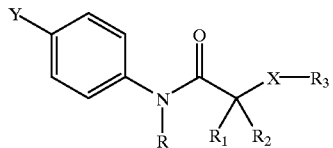

(I)

wherein
Y is halogen, $C_1$–$C_4$alkyl, $C_1$–$C_4$haloalkyl, $C_1$–$C_4$alkoxy, $C_1$–$C_4$haloalkoxy, nitro or cyano;
R is hydrogen,
  $C_1$–$C_4$alkyl optionally substituted with one $C_1$–$C_4$alkoxy group, or
  benzoyl optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;
$R_1$ is $C_1$–$C_4$alkyl and $R_2$ is $C_1$–$C_4$alkyl, halogen or hydrogen, or $R_1$ and $R_2$ may be taken together with the carbon atom to which they are attached to form a cyclopropyl ring;
X is

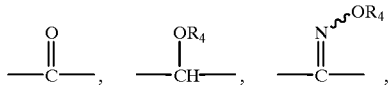

O or $S(O)_n$;
n is an integer of 0, 1 or 2;
$R_3$ is $C_3$–$C_6$cycloalkyl, or
  $C_1$–$C_6$alkyl optionally substituted with one phenyl ring wherein the phenyl ring is optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;
$R_4$ is hydrogen, $C_1$–$C_8$alkyl, $C_1$–$C_8$haloalkyl, $C_1$–$C_6$acyl, $C_1$–$C_6$haloacyl, $C_1$–$C_4$alkoxymethyl, $C_3$–$C_6$cycloalkyl, $C_3$–$C_6$alkenyl, $C_3$–$C_6$alkynyl or $S(O)_nR_5$; and
$R_5$ is $C_1$–$C_4$alkyl or $C_1$–$C_4$haloalkyl; and the optical isomers, tautomers, agriculturally acceptable salts and agriculturally acceptable metal chelates thereof.

This invention also comprises compositions containing those compounds and methods for using those compounds and compositions. Advantageously, it has been found that the substituted anilide compounds of the present invention, and compositions containing them, are useful for the control of insect pests. The compounds of this invention are also useful for the protection of plants from damage caused by insect attack and infestation.

DETAILED DESCRIPTION OF THE INVENTION

The present invention provides a method for the control of insect pests which comprises contacting said pests, or their food supply, habitat or breeding grounds with a pesticidally effective amount of a substituted anilide compound of formula I.

The present invention also provides a method for the protection of growing plants from attack or infestation by insect pests which comprises applying to the foliage of the plants, or to the soil or water in which they are growing or are to be grown, a pesticidally effective amount of a substituted anilide compound of formula I.

Insecticidal substituted anilide compounds of the present invention have the structural formula I

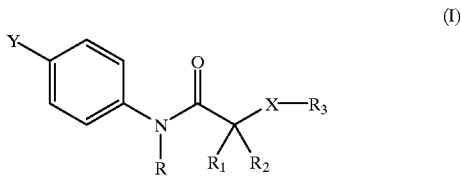

(I)

wherein R, $R_1$, $R_2$, $R_3$, X and Y are as described hereinabove for formula I.

Exemplary of halogen hereinabove are fluorine, chlorine, bromine and iodine. The terms "$C_1$–$C_4$haloalkyl", "$C_1$–$C_8$haloalkyl", "$C_1$–$C_4$haloalkoxy" and "$C_1$–$C_6$haloacyl" are defined as a $C_1$–$C_4$alkyl group, a $C_1$–$C_8$alkyl group, a $C_1$–$C_4$alkoxy group and a $C_1$–$C_6$acyl group substituted with one or more halogen atoms, respectively. Agriculturally acceptable salts of formula I compounds include, but are not limited to, acid addition salts formed from acids such as hydrochloric acid, sulfuric acid and phosphoric acid, and basic salts such as pyridine salts, alkali metal salts and alkaline earth metal salts. In addition, formula I compounds wherein X is

may form chelates with boron, transition metals such as copper and zinc, and lanthanide metals.

Advantageously, it has been found that the substituted anilide compounds of the present invention are especially useful for the control of soil-dwelling Coleoptera pests such as southern corn rootworms, northern corn rootworms, western corn rootworms, and Mexican corn rootworms.

Preferred formula I compounds of the present invention are those wherein

Y is halogen or $C_1$–$C_4$haloalkyl;

R is hydrogen,
  $C_1$–$C_4$alkyl optionally substituted with one $C_1$–$C_4$alkoxy group, or
  benzoyl optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;

$R_1$ and $R_2$ are each independently $C_1$–$C_4$alkyl;

X is

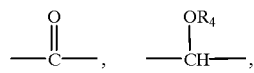

O or $S(O)_n$;

n is an integer of 1 or 2;

$R_3$ is $C_1$–$C_6$alkyl; and $R_4$ is $C_6$–$C_8$alkyl, $C_1$–$C_6$acyl, $C_1$–$C_4$alkoxymethyl, $C_3$–$C_6$alkenyl or $C_3$–$C_6$alkynyl.

More preferred insecticidal agents of the present invention are those wherein

Y is Cl or trifluoromethyl;

R is hydrogen, $C_1$–$C_4$alkyl, $C_1$–$C_4$alkoxymethyl, or
  benzoyl optionally substituted with one or more groups independently selected from halogen, $C_1$–$C_4$alkyl, $C_1$–$C_4$haloalkyl, $C_1$–$C_4$alkoxy or $C_1$–$C_4$haloalkoxy groups;

$R_1$ and $R_2$ are methyl;

X is

O or $S(O)_n$;

n is an integer of 1 or 2;

$R_3$ is isopropyl or tert-butyl; and $R_4$ is $C_1$–$C_4$alkyl, $C_2$–$C_6$acyl, $C_1$–$C_4$alkoxymethyl, allyl or propargyl.

Most preferred substituted anilide compounds of this invention are those wherein Y is Cl or trifluoromethyl;

R is hydrogen, $C_1$–$C_4$alkyl or $C_1$–$C_4$alkoxymethyl;

$R_1$ and $R_2$ are methyl;

X is

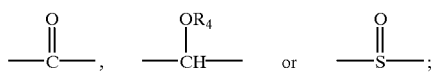

$R_3$ is isopropyl; and $R_4$ is $C_2$–$C_6$acyl.

Formula I compounds of this invention which are particularly effective for the control of soil-dwelling Coleoptera pests include α,α,α-trifluoro-2,2,4-trimethyl-3-oxo-p-valerotoluidide;

α,α,α-trifluoro-2-(isopropylsulfinyl)-2-methyl-p-propionotoluidide;

4'-chloro-3-hydroxy-2,2,4-trimethylvaleranilide, acetate (ester);

α,α,α-trifluoro-N,2,2,4-tetramethyl-3-oxo-p-valerotoluidide; and

N-(ethoxymethyl)-α,α,α-trifluoro-2,2,4-trimethyl-3-oxo-p-valerotoluidide, among others.

Novel substituted anilide compounds of the present invention have the structural formula I

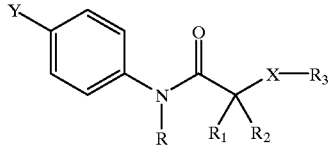

wherein R, $R_1$, $R_2$, $R_3$, X and Y are as described hereinabove for formula I provided that Y cannot be methyl or methoxy when X is

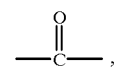

R is hydrogen, $R_1$ and $R_2$ are methyl, and $R_3$ is isopropyl.

Formula I compounds wherein X is C(O) may be prepared, as shown in Flow Diagram I, by reacting a substituted aniline of formula II with an acid chloride of formula III in the presence of a base.

FLOW DIAGRAM I

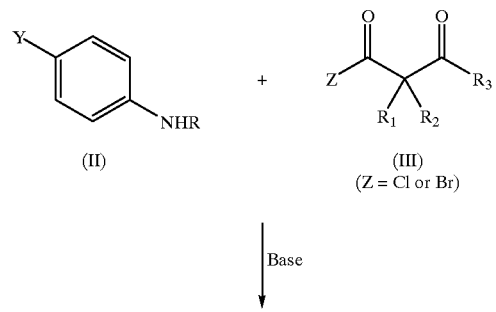

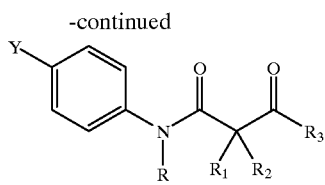

Certain substituted anilide compounds wherein R is other than hydrogen may be prepared, as shown in Flow Diagram II, by reacting a formula I compound wherein R is hydrogen with an electrophile of formula IV in the presence of a base.

FLOW DIAGRAM II

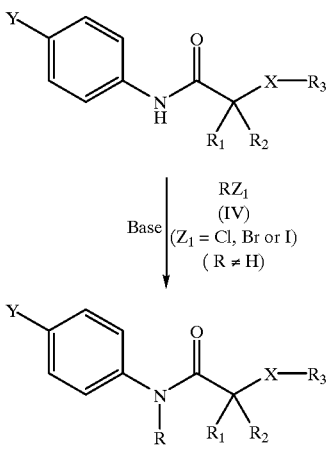

Formula I compounds wherein X is O may be prepared, as shown in Flow Diagram III, by reacting a substituted aniline of formula II with an a-bromoacid halide of formula V in the presence of a base to form an intermediate compound of formula VI, and reacting the intermediate compound with an alcohol of formula VII in the presence of silver oxide.

FLOW DIAGRAM III

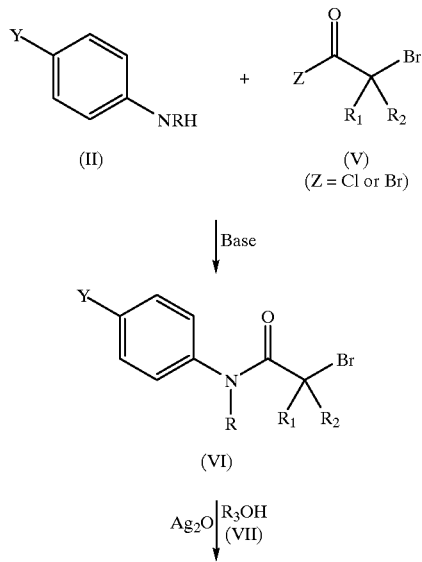

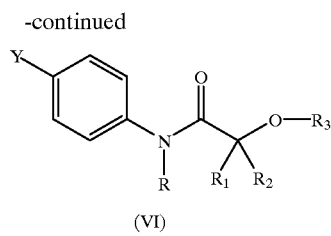

(VI)

Formula I compounds wherein $R_1$ and $R_2$ are taken together to form a cyclopropyl group and X is C(O) may be prepared, as shown in Flow Diagram IV, by reacting a β-ketoester of formula VIII with benzyltriethylammonium chloride, aqueous sodium hydroxide and 1,2-dibromoethane to form an intermediate compound which is acidified with hydrochloric acid to form an acid of formula IX, reacting the formula IX acid with oxalyl chloride to form an acid chloride of formula X, and reacting the acid chloride with a substituted aniline of formula II in the presence of a base.

FLOW DIAGRAM IV

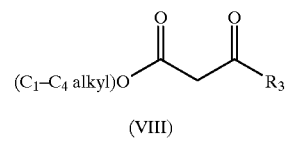

(VIII)

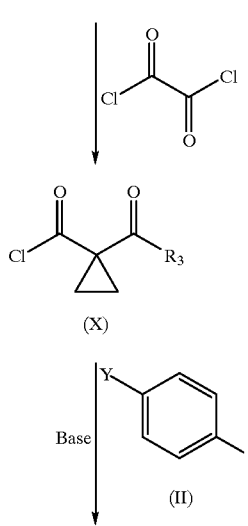

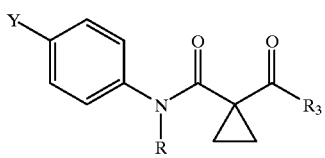

Certain substituted anilide compounds wherein X is C(O) and $R_2$ is hydrogen or halogen may be prepared, as shown in Flow Diagram V, by reacting a substituted aniline of formula II with a β-ketoester of formula VIII to form an intermediate compound of formula XI, and reacting the formula XI compound with an alkylhalide of formula XII to form a formula I compound wherein $R_2$ is hydrogen, and optionally reacting the formula I compound wherein $R_2$ is hydrogen with a sulfuryl halide to form a formula I compound wherein $R_2$ is halogen.

FLOW DIAGRAM V

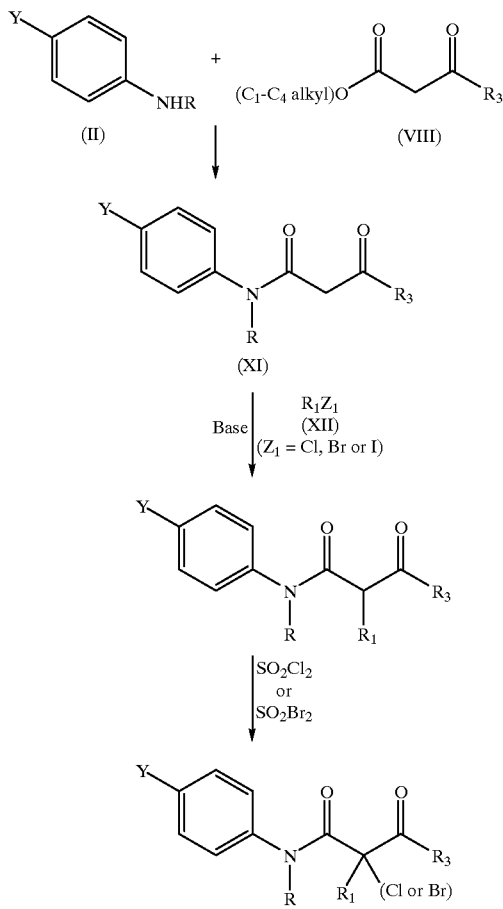

Compounds of formula I wherein $R_1$ and $R_2$ are $C_1$–$C_4$alkyl and X is C(O) may be prepared, as shown in Flow Diagram VI, by reacting a substituted aniline compound of formula II with a lactone of formula XIII.

FLOW DIAGRAM VI

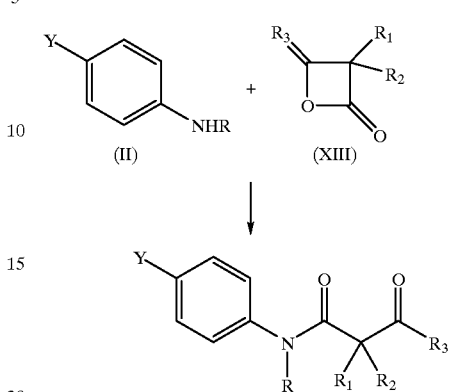

Formula I compounds wherein X is CH($OR_4$) may be prepared, as shown in Flow Diagram VII, by reducing a formula I compound wherein X is C(O) with a conventional reducing agent such as sodium borohydride to form the corresponding formula I compound wherein X is CH(OH), and optionally reacting the formula I compound wherein X is CH(OH) with an electrophile of formula XIV in the presence of a base.

FLOW DIAGRAM VII

Certain formula I compounds wherein X is C(=$NOR_4$) may be prepared, as shown in Flow Diagram VIII, by reacting a formula I compound wherein X is C(O) with an optionally substituted hydroxylamine hydrochloride of formula XV in the presence of a base.

FLOW DIAGRAM VIII

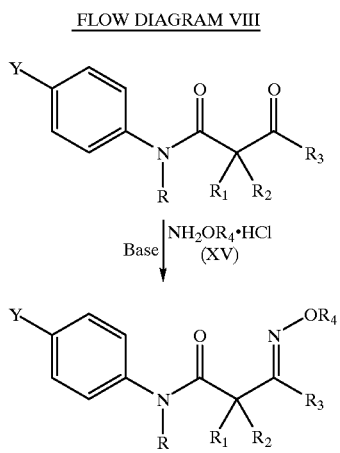

Formula I compounds wherein X is $S(O)_n$ may be prepared, as shown in Flow Diagram IX, by reacting a substituted acetic acid of formula XVI with thionyl chloride to form an acid chloride of formula XVII, reacting the acid chloride with a substituted aniline of formula II in the presence of a base to form a formula I compound wherein X is S, and optionally oxidizing the formula I compound wherein X is S with a conventional oxidizing agent to form formula I compounds wherein X is $S(O)_n$ and n is 1 or 2.

FLOW DIAGRAM IX

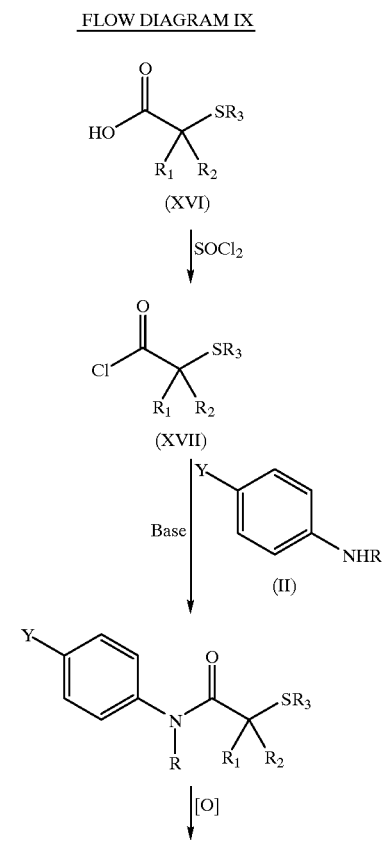

Other methods for the preparation of formula I compounds will become apparent from the examples set forth below. In addition, certain compounds of formula I may be converted into other compounds of formula I using conventional procedures known to those skilled in the art.

The substituted anilide compounds of the present invention are particularly useful for the control of Coleoptera pests including, but not limited to, Chrysomelidae such as *Diabrotica undecimpunctata* (southern corn rootworm), *Diabrotica barberi* (northern corn rootworm), *Diabrotica virgifera* (western and Mexican corn rootworms) and *Diabrotica balteata* (banded cucumber beetle), Elateridae such as *Limonius californicus* (sugarbeet wireworm), *Agriotes mancus* (wheat wireworm) and *Conoderus falli* (potato wireworm), Scarabaeidae such as *Popillia japonica* (Japanese beetle), and Carabidae such as *Stenolophus lecontei* (seedcorn beetle). The formula I compounds of this invention are especially useful for the control of soil-dwelling Coleoptera pests such as southern corn rootworm, northern corn rootworm, western corn rootworm, and Mexican corn rootworm.

The formula I compounds of this invention are useful for protecting crop plants and turfgrasses from insect attack and infestation. In particular, the formula I compounds of this invention are useful for protecting corn, potato, sugarbeet, wheat, sugarcane, peanut and soybean crops, and turfgrasses from soil-dwelling Coleoptera attack and infestation. The compounds of this invention are especially useful for protecting corn from southern corn rootworm, northern corn rootworm, western corn rootworm, and Mexican corn rootworm attack and infestation.

The substituted anilide compounds of this invention are effective for controlling insect pests when applied to the foliage of plants and/or to the soil or water in which said plants are growing or are to be grown in sufficient amount to provide a rate of about 0.1 kg/ha to 50 kg/ha, preferably about 0.1 kg/ha to 10 kg/ha, more preferably about 0.5 kg/ha to 2 kg/ha, of active ingredient. The compounds of the present invention are especially useful for protecting crop plants and turfgrasses from soil-dwelling Coleoptera attack and infestation when the compounds are applied to the soil in which the crops and turfgrasses are growing or are to be grown in sufficient amount to provide a rate of about 0.1 kg/ha to 50 kg/ha, preferably about 0.1 kg/ha to 10 kg/ha, of active ingredient.

While the compounds of this invention are effective for controlling insect pests when employed alone, they may also be used in combination with other biological chemicals, including other insecticides. For example, the formula I compounds of this invention may be used effectively in conjunction or combination with pyrethroids, phosphates, carbamates, cyclodienes, endotoxin of *Bacillus thuringiensis* (Bt), formamidines, phenol tin compounds, chlorinated hydrocarbons, benzoylphenyl ureas, pyrroles and the like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a compound of the invention (or combinations thereof) admixed with one or more agronomically acceptable inert, solid or liquid carriers. Those compositions contain a pesticidally effective amount of said compound or compounds, which may vary depending upon the particular compound, target pest, and method of use. Those skilled in the art can readily determine what is a pesticidally effective amount without undue experimentation.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of α,α,α-Trifluoro-2,2,4-trimethyl-3-oxo-p-valerotoluidide

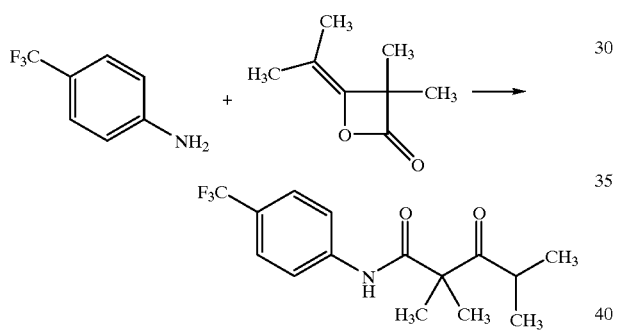

A mixture of α,α,α-trifluoromethyl-p-toluidine (4.83 g, 0.03 mol) and 3-hydroxy-2,2,4-trimethyl-3-pentenoic acid-β-lactone (4.2 g, 0.03 mol) is heated at 100° until infrared analysis indicates the disappearance of the lactone. The crude product is recrystallized from ether to give the title product as a solid (4.4 g, mp 120.5–122° C.).

Using essentially the same procedure, but using the appropriately substituted aniline or N-methylaniline, the following compounds are obtained.

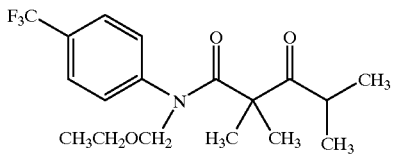

| R | mp ° C. |
|---|---|
| H | 105–108 |
| CH₃ | |

EXAMPLE 2

Preparation of α,α,α-Trifluoro-N,2,2,4-tetramethyl-3-oxo-p-valerotoluidide

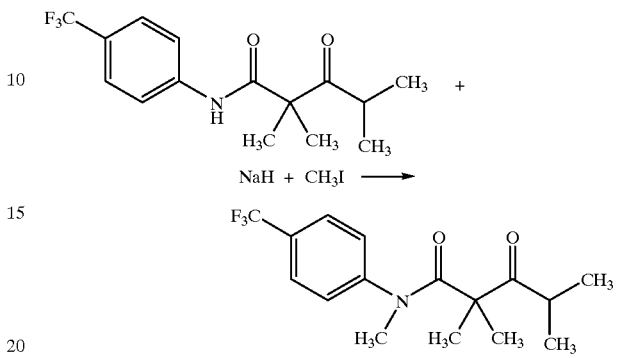

A solution of α,α,α-trifluoro-2,2,4-trimethyl-3-oxo-p-valerotoluidide (5.0 g, 0.016 mol) in tetrahydrofuran is treated sequentially with sodium hydride (60% mineral oil dispersion, 0.79 g, 0.019 mol) at 15–20° C. and iodomethane (2.83 g, 0.02 mol). The reaction is followed by gas chromatography and when it is complete (87% product by gas chromatography) the reaction mixture is poured into water and extracted with ether. Column chromatography of the crude product using silica gel and a hexanes/ethyl acetate solution (4:1) affords an oil which crystallizes to give the title product as a white solid, mp 54–56° C.

Using essentially the same procedure, the following compound is obtained:

EXAMPLE 3

Preparation of α,α,α,α',α',α'-Hexafluoro-N-(2,2,4-trimethyl-3-oxovaleryl)-p-tolu-p-toluidide

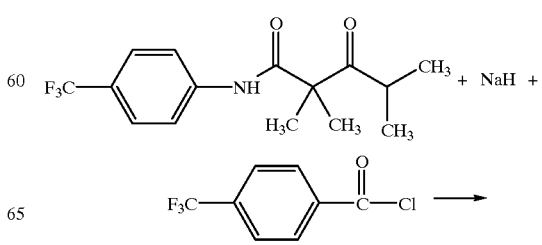

-continued

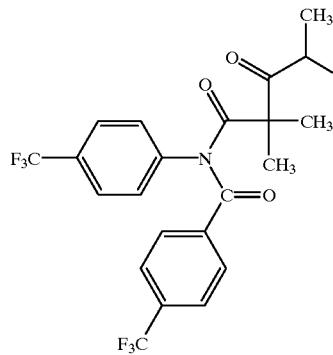

A solution of α,α,α-trifluoro-2,2,4-trimethyl-3-oxo-p-valerotoluidide (3.01 g, 0.01 mol) in tetrahydrofuran is chilled to 10° C., treated with sodium hydride (50% in oil, 0.480 g, 0.01 mol), stirred for 30 minutes at 10° C., treated with p-trifluoromethylbenzoyl chloride (2.5 g, 0.01 mol), stirred for 3.5 hours at room temperature, concentrated in vacuo, and diluted with ethyl acetate. The resultant solution is washed sequentially with water, 5% sodium hydroxide solution and brine, dried over anhydrous sodium sulfate, and concentrated in vacuo to obtain a solid. The solid is recrystallized from a benzene/hexanes solution and hexanes to give the title product as a solid (mp 116–118° C.)

Using essentially the same procedure, the following compounds are obtained:

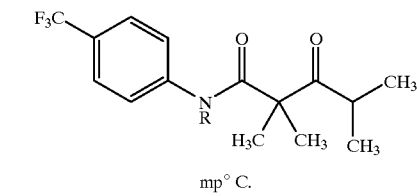

mp° C.          R

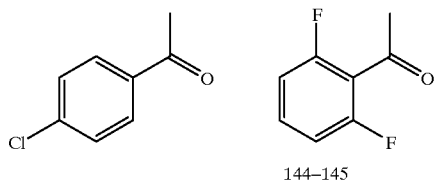

144–145

EXAMPLE 4

Preparation of α,α,α-Trifluoro-2,2,4,4-tetramethyl-3-oxo-p-valerotoluidide

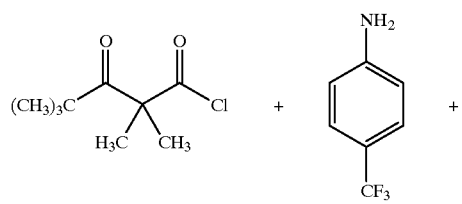

-continued

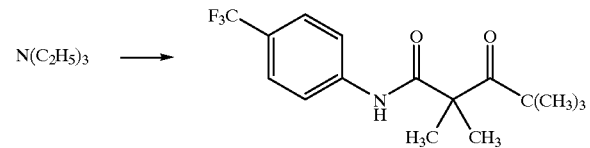

To an ice-bath cooled solution of 4-trifluoromethylaniline (0.84 g, 5.2 mmol) and triethylamine (0.73 mL, 5.2 mmol) in ether is added dropwise over a period of 15 minutes a solution of 2,2,4,4-tetramethyl-3-oxo-valeryl chloride (1.0 g, 5.2 mmol) in ether. After stirring overnight at room temperature, the reaction mixture is diluted with ether, washed sequentially with 5% aqueous hydrochloric acid and brine, dried over anhydrous magnesium sulfate, and concentrated in vacuo to obtain a white solid. The solid is recrystallized from hexanes to give the title product as a white solid (1.20 g, mp 122–124° C.) which is identified by $^1$H NMR spectral analysis.

EXAMPLE 5

Preparation of 2-Bromo-α,α,α-trifluoro-2-methyl-p-propionotoluidide

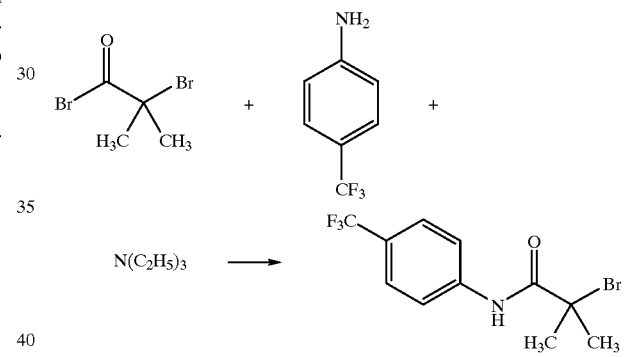

To an ice-bath cooled solution of 4-trifluoromethylaniline (3.50 g, 0.0217 mol) and triethylamine (3.03 mL, 0.0217 mol) in ether is added dropwise over a period of 10 minutes a solution of 2-bromoisobutyryl bromide (5.0 g, 0.0217 mol) in ether. After stirring overnight at room temperature, the insolubles that form are removed by filtration. The filtrate is washed sequentially with 5 aqueous hydrochloric acid and brine, dried over anhydrous magnesium sulfate, and concentrated in vacuo to obtain a white solid. The solid is recrystallized from hexanes to give the title product as a white solid (5.46 g, mp 113–115° C.) which is identified by $^1$H NMR spectral analysis.

EXAMPLE 6

Preparation of 2-Ethoxy-α,α,α-trifluoro-2-methyl-p-propionotoluidide

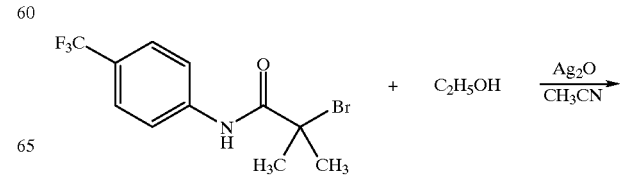

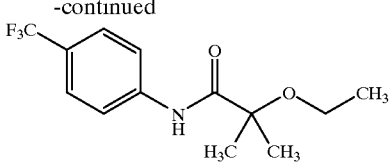

A mixture of 2-bromo-α,α,α-trifluoro-2-methyl-p-propionotoluidide (1.0 g, 3.2 mmol), ethanol (0.21 mL, 3.6 mmol) and silver oxide (0.75 g, 3.2 mmol) in acetonitrile is stirred at room temperature. After 5 days, the mixture is filtered through a pad of diatomaceous earth and the filtrate is concentrated in vacuo. Flash column chromatography of the residue using silica gel and an ethyl acetate/hexanes solution (1:5) gives the title product as a white solid (0.64 g, mp 58–61° C.) which is identified by $^1$H NMR spectral analysis.

Using essentially the same procedure, the following compounds are obtained:

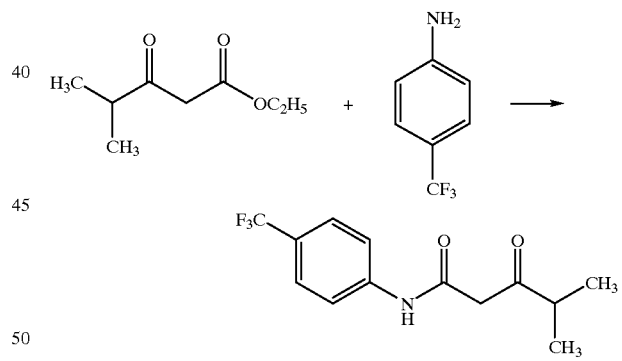

| $R_3$ | mp ° C. |
|---|---|
| C(CH$_3$)$_3$ | 93–94 |
| CH(CH$_3$)$_2$ | 36–43 |

EXAMPLE 7

Preparation of α,α,α-Trifluoro-1-isobutyrylcyclopropanecarboxy-p-toluidide

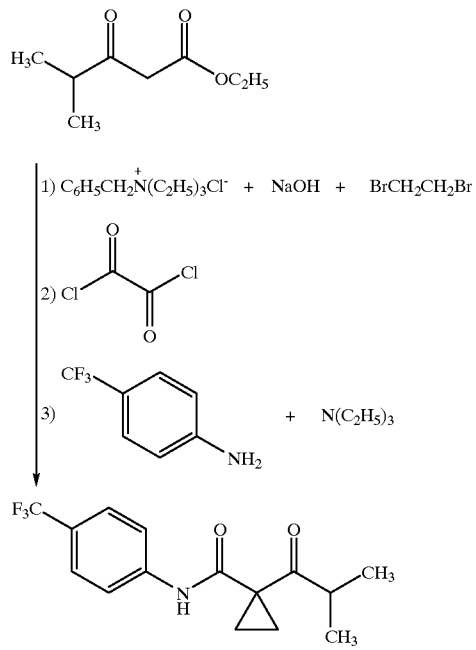

A mixture of ethyl isobutyrylacetate (0.79 g, 5 mmol), benzyltriethylammonium chloride (0.57 g, 2.5 mmol), 1,2-dibromoethane (0.86 g, 10 mmol) and 50% aqueous sodium hydroxide (10 mL) is heated at 60° C. After 2.5 hours, the reaction mixture is cooled to room temperature and diluted with water. The aqueous mixture is washed with ether, acidified with concentrated hydrochloric acid, and extracted with ether. The combined organic extracts are washed with brine, dried over anhydrous magnesium sulfate, and concentrated in vacuo to obtain a yellow liquid. The liquid is dissolved in methylene chloride and treated with oxalyl chloride (0.33 mL, 3.7 mmol) and 1 drop of N,N-dimethylformamide. After stirring for two hours at room temperature, the reaction mixture is concentrated in vacuo to afford the acid chloride as a yellow liquid. A solution of the acid chloride in ether is added dropwise over a period of 5 minutes to an ice-bath cooled solution of triethylamine (0.57 mL, 4.1 mmol) and p-trifluoromethylaniline (0.51 mL, 4.1 mmol) in ether. After stirring overnight at room temperature, the mixture is diluted with ether, washed sequentially with 5% aqueous hydrochloric acid and brine, dried over anhydrous magnesium sulfate, and concentrated in vacuo to obtain a residue. Flash column chromatography of the residue using silica gel and an ethyl acetate/hexanes solution (1:5) gives the title product as a white solid (0.61 g, mp 79–82° C.) which is identified by $^1$H NMR spectral analysis.

EXAMPLE 8

Preparation of α,α,α-Trifluoro-4-methyl-3-oxo-p-valerotoluidide

A mixture of ethyl isobutyrylacetate (2.0 g, 0.0126 mol) and p-trifluoromethylaniline is heated at 100° C. After 2 days, the reaction mixture is cooled to room temperature, diluted with ether, washed sequentially with 10% aqueous hydrochloric acid and brine, dried over anhydrous magnesium sulfate, and concentrated in vacuo to obtain an amber syrup. Flash column chromatography of the syrup using silica gel and an ethyl acetate/hexanes solution (1:4) gives the title product as a pale yellow syrup (1.35 g) which is identified by $^1$H NMR spectral analysis.

EXAMPLE 9

Preparation of α,α,α-Trifluoro-2,4-dimethyl-3-oxo-p-valerotoluidide

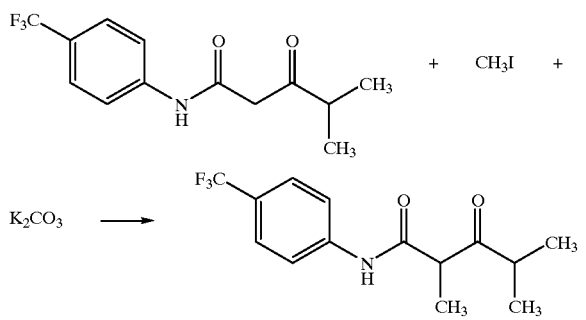

A mixture of α,α,α-trifluoro-4-methyl-3-oxo-p-valerotoluidide (1.34 g, 4.9 mmol), potassium carbonate (0.68 g, 4.9 mmol) and iodomethane (0.34 mL, 5.4 mmol) in acetone is stirred at room temperature for 4 hours, concentrated in vacuo, and partitioned between dilute hydrochloric acid and ether. The organic phase is separated, washed with brine, dried over anhydrous magnesium sulfate, and concentrated in vacuo to obtain a solid. The solid is recrystallized from hexanes to give the title product as an off-white solid (0.95 g, mp 109–112° C.) which is identified by $^1$H NMR spectral analysis.

EXAMPLE 10

Preparation of 2-Chloro-α,α,α-trifluoro-2,4-dimethyl-p-valerotoluidide

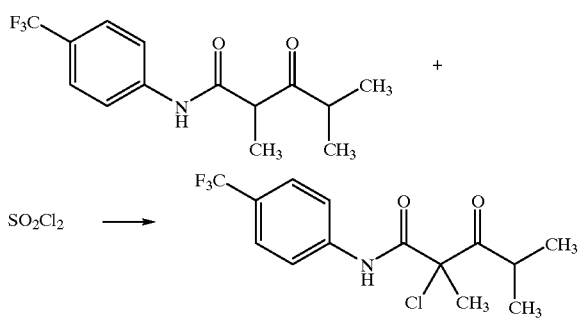

A solution of α,α,α-trifluoro-2,4-dimethyl-3-oxo-p-valerotoluidide (0.67 g, 2.3 mmol) and sulfuryl chloride (0.20 mL, 2.5 mmol) in methylene chloride is stirred at room temperature for 4 hours, diluted with methylene chloride, washed sequentially with water and brine, dried over anhydrous magnesium sulfate, and concentrated in vacuo to obtain a solid. The solid is recrystallized from hexanes to give the title product as a white solid (0.59 g, mp 119–122° C.) which is identified by $^1$H NMR spectral analysis.

EXAMPLE 11

Preparation of α,α,α-Trifluoro-3-hydroxy-2,2,4-trimethyl-p-valerotoluidide

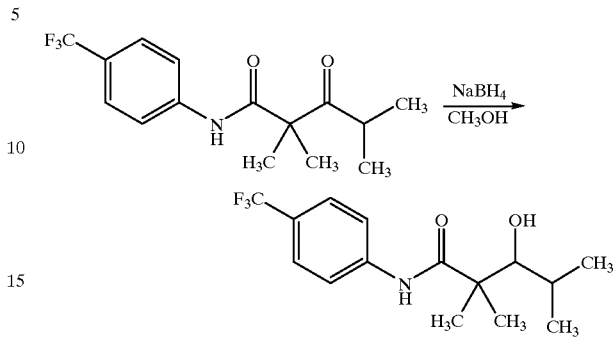

A cooled (ice-bath) solution of α,α,α-trifluoro-2,2,4-trimethyl-3-oxo-p-valerotoluidide (20.0 g, 0.0664 mol) in methanol is treated portionwise with sodium borohydride (2.51 g, 0.0664 mol), warmed to and stirred at room temperature for 2 hours, treated with 10% hydrochloric acid (40 mL), and poured into water. The resultant aqueous mixture is filtered to obtain the title product as a white solid (19.38 g) which is identified by $^1$H NMR spectral analysis.

Using essentially the same procedure, the following compound is obtained:

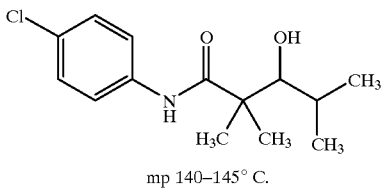

mp 140–145° C.

EXAMPLE 12

Preparation of 3-(Allyloxy)-α,α,α-trifluoro-2,2,4-trimethyl-p-valerotoluidide

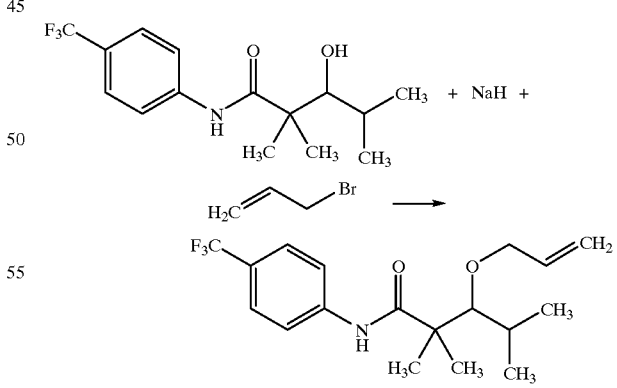

A suspension of sodium hydride (0.44 g of a 60% dispersion in mineral oil, 10.9 mmol) in tetrahydrofuran is treated dropwise with a solution of α,α,α-trifluoro-3-hydroxy-2,2,4-trimethyl-p-valerotoluidide (3.0 g, 9.9 mmol) in tetrahydrofuran, stirred for 20 minutes at room temperature, treated with a solution of allyl bromide in tetrahydrofuran, stirred for 18 hours at room temperature and 18 hours at 50° C., concentrated in vacuo, and diluted with ethyl acetate. The organic solution is washed sequentially with water and brine, dried over anhydrous magnesium sulfate, and concentrated in vacuo to obtain a yellow syrup. Flash column chromatography of the syrup using silica gel and an ethyl acetate/hexanes solution (1:10) gives the title product as a white solid (1.72 g, mp 47–52° C.) which is identified by $^1$H NMR spectral analysis.

Using essentially the same procedure, the following compounds are obtained:

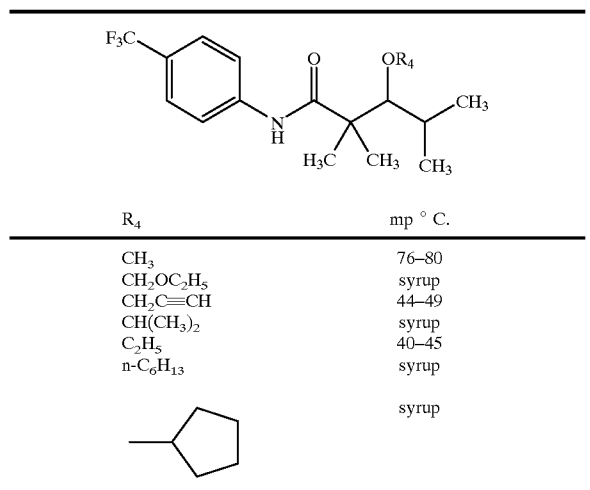

| R$_4$ | mp ° C. |
|---|---|
| CH$_3$ | 76–80 |
| CH$_2$OC$_2$H$_5$ | syrup |
| CH$_2$C≡CH | 44–49 |
| CH(CH$_3$)$_2$ | syrup |
| C$_2$H$_5$ | 40–45 |
| n-C$_6$H$_{13}$ | syrup |
|  | syrup |

EXAMPLE 13

Preparation of 3-Hydroxy-α,α,α-trifluoro-2,2,4-trimethyl-p-valerotoluidide, chloroacetate (ester)

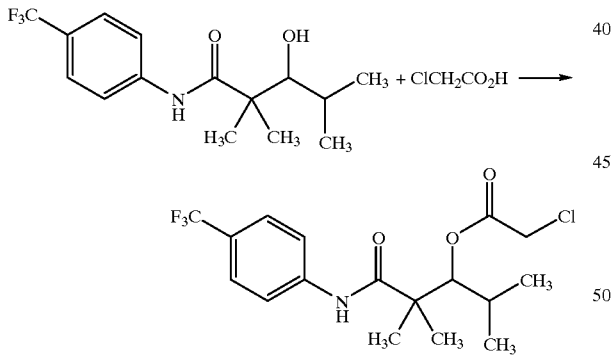

To a stirred solution of α,α,α-trifluoro-3-hydroxy-2,2,4-trimethyl-p-valerotoluidide (1.0 g, 3.3 mmol), chloroacetic acid (0.37 g, 4.0 mmol) and dimethylaminopyridine (0.04 g, 0.33 mmol) in methylene chloride is added dropwise a solution of dicyclohexylcarbodiimide (0.82 g, 4.0 mmol) in methylene chloride over a period of 10 minutes. After stirring overnight at room temperature, the reaction mixture is filtered to remove insolubles and the filtrate is concentrated in vacuo to afford a white solid. Flash column chromatography of the solid using silica gel and an ethyl acetate/hexanes solution (1:7) gives the title product as a white solid (1.14 g, mp 108–110° C.) which is identified by $^1$H NMR spectral analysis.

EXAMPLE 14

Preparation of 3-(Difluoromethoxy)-α,α,α-trifluoro-2,4-dimethyl-p-valerotoluidide and α,α,α-Trifluoro-3-hydroxy-2,2,4-trimethyl-p-valerotoluidide, formate (ester)

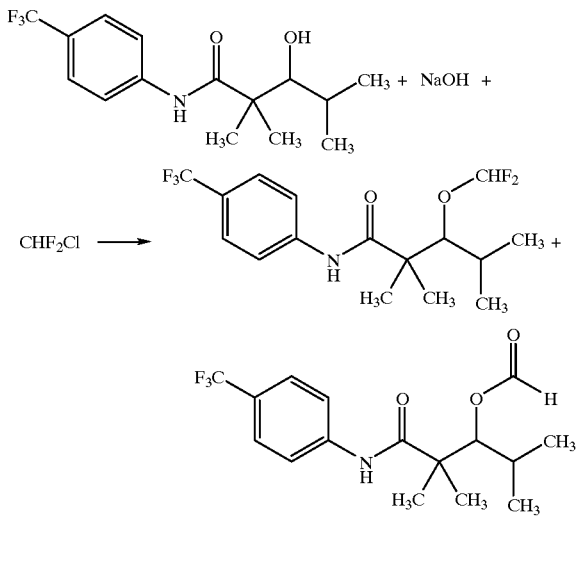

A mixture of α,α,α-trifluoro-3-hydroxy-2,2,4-trimethyl-p-valerotoluidide (2.0 g, 6.6 mmol), difluorochloromethane (1.71 g, 19.8 mmol), 50% aqueous sodium hydroxide (1.58 g, 19.8 mmol) and N,N-dimethylacetamide is placed in a pressure tube and stirred at room temperature. After 1 day, additional difluorochloromethane (0.57 g, 6.6 mmol) and 50% sodium hydroxide (0.53 g, 6.6 mmol) are added and stirring is continued for 3 days. The reaction mixture is then diluted with water and extracted with ether. The combined organic extracts are washed with brine, dried over anhydrous magnesium sulfate, and concentrated in vacuo to obtain a clear syrup. Flash column chromatography of the syrup using silica gel and an ethyl acetate/hexanes solution (1:7) gives the title products as clear syrups. Both products are identified by $^1$H NMR spectral analysis.

EXAMPLE 15

Preparation of α,α,α-Trifluoro-3-hydroxy-2,2,4-trimethyl-p-valerotoluidide, methanesulfonate (ester)

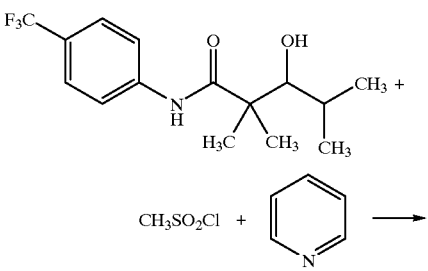

-continued

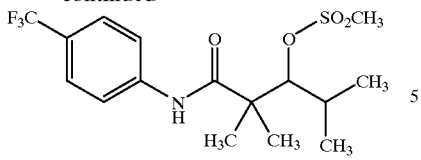

A solution of α,α,α-trifluoro-3-hydroxy-2,2,4-trimethyl-p-valerotoluidide (1.0 g, 3.3 mmol) and methanesulfonyl chloride (0.38 mL, 4.9 mmol) in pyridine is stirred at room temperature for 19 hours, treated with additional methanesulfonyl chloride (0.13 mL, 1.7 mmol), stirred at room temperature for 24 hours, and poured into 5% hydrochloric acid. The resultant aqueous mixture is extracted with ethyl acetate. The combined organic extracts are washed sequentially with 5% aqueous sodium hydroxide and brine, dried over anhydrous magnesium sulfate, and concentrated in vacuo to obtain a yellow syrup. Flash column chromatography of the syrup using silica gel and an ethyl acetate/hexanes solution (1:4) gives the title product as a clear syrup (0.78 g) which is identified by $^1$H NMR spectral analysis.

EXAMPLE 16

Preparation of 4'-Chloro-3-methoxy-2,2,4-trimethyl-valeranilide

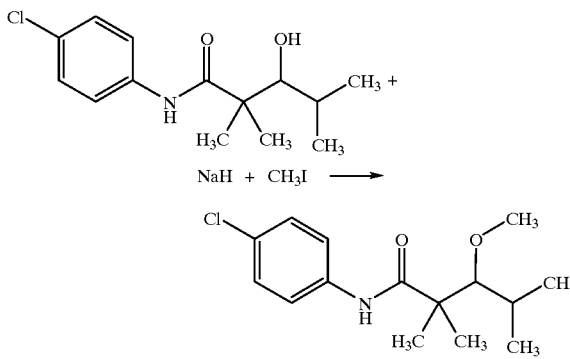

To a stirred suspension of sodium hydride (0.25 g of a 60% dispersion in mineral oil, 5.1 mmol) in N,N-dimethylacetamide is added dropwise a solution of 4'-chloro-3-hydroxy-2,2,4-trimethylvaleranilide (1.5 g, 5.6 mmol) in N,N-dimethylacetamide. After stirring for 40 minutes at room temperature, iodomethane (1.58 g, 11.1 mmol) is added. The reaction mixture is stirred at room temperature for 18 hours, diluted with water, and extracted with ether. The combined organic extracts are washed with brine, dried over anhydrous magnesium sulfate, and concentrated in vacuo to obtain a semisolid. Flash column chromatography of the semi-solid using silica gel and an ethyl acetate/hexanes solution (1:10) gives the title product as a white solid (0.71 g, mp 103–107° C.) which is identified by $^1$H NMR spectral analysis.

EXAMPLE 17

Preparation of α,α,α-Trifluoro-3-hydroxy-2,2,4-trimethyl-p-valerotoluidide, acetate (ester)

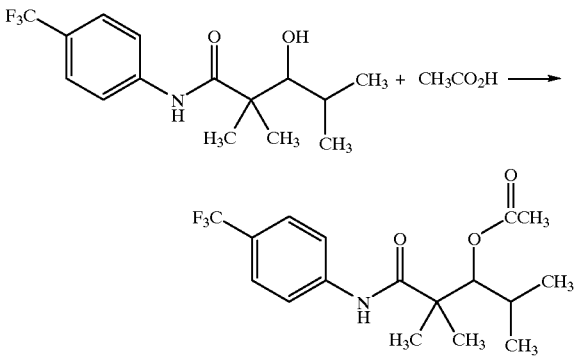

A solution of α,α,α-trifluoro-3-hydroxy-2,2,4-trimethyl-p-valerotoluidide (2.38 g, 0.008 mol), acetic acid (0.48 g, 0.08 mol) and a few crystals of 4-dimethyl-aminopyridine in methylene chloride is treated with dicyclohexylcarbodiimide (1.65 g, 0.008 mol). After stirring overnight, the reaction mixture is filtered and the resultant filtrate is concentrated in vacuo to obtain a residue. The residue is crystallized from hexanes to give the title product as a white solid (2.1 g, mp 116.0–120.0° C.).

EXAMPLE 18

Preparation of α,α,α-Trifluoro-2,2,4-trimethyl-3-oxo-p-valerotoluidide, 3-oxime

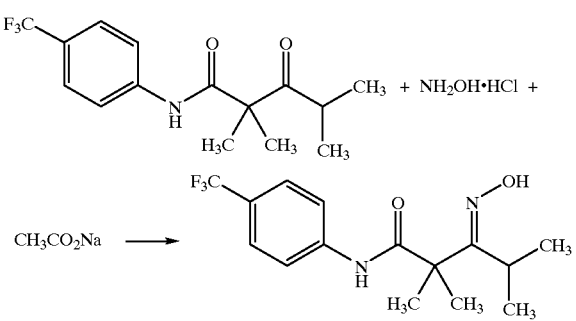

A mixture of α,α,α-trifluoro-2,2,4-trimethyl-3-oxo-p-valerotoluidide (3.0 g, 0.01 mol), hydroxylamine hydrochloride (3.47 g, 0.05 mol) and sodium acetate (4.1 g, 0.05 mol) in dioxane is refluxed for 18 hours, cooled, and filtered. The resultant filtrate is concentrated in vacuo to obtain a sticky solid which is triturated with hexanes to give the title product as a white solid (0.356 g, mp 175–177°C.).

EXAMPLE 19

Preparation of α,α,α-Trifluoro-2,2,4-trimethyl-3-oxo-4-phenyl-p-valerotoluidide

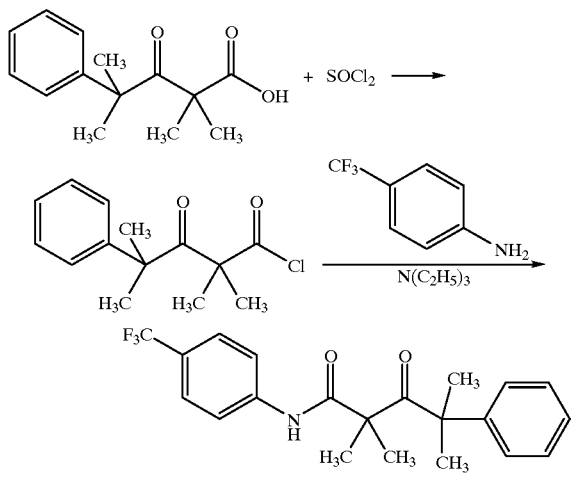

A solution of 2,2,4-trimethyl-3-oxo-4-phenylvaleric acid (2.34 g, 0.01 mol) and thionyl chloride (1.31 g, 0.011 mol) in toluene and a drop of N,N-dimethylformamide is refluxed for 2 hours, concentrated in vacuo, and diluted with tetrahydrofuran. Half of the solution (0.005 mol) is added to a solution of p-trifluoromethyl-aniline (0.805 g, 0.005 mol) and triethylamine (0.607 g, 0.006 mol) in tetrahydrofuran. The resultant mixture is stirred for 4 hours at room temperature, quenched with water, and extracted with ether. The organic extract is washed sequentially with dilute hydrochloric acid, water, dilute sodium hydrogen carbonate solution and water, and concentrated in vacuo to obtain a residue. The residue is crystallized from a benzene/hexanes solution to give the title product as an off-white solid (1.6 g, mp 147.0–148.5° C.).

EXAMPLE 20

Preparation of α,α,α-Trifluoro-2-(isopropylsulfinyl)-2-methyl-p-propionotoluidide

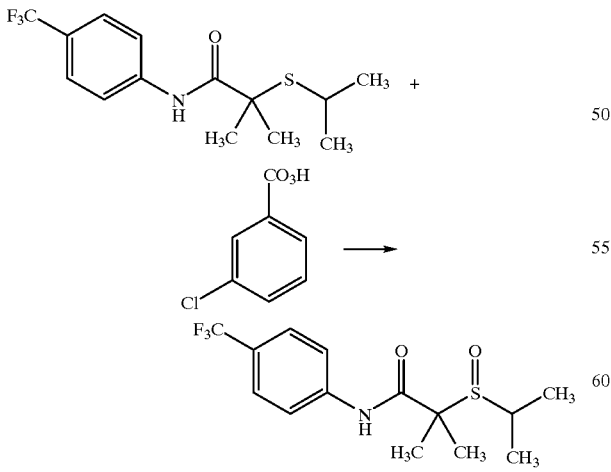

solution of α,α,α-trifluoro-2-(isopropylthio)-2-methyl-p-propionotoluidide (3.05 g, 0.01 mol) in ethyl acetate is treated with a solution of m-choroperoxybenzoic acid (1.90 g real) in ethyl acetate at 5° C. over 30 minutes, stirred for two hours at 5° C., and diluted with ether. The resultant organic solution is washed sequentially with aqueous sodium carbonate solution and water, and concentrated in vacuo to obtain a residue. The residue is crystallized from petroleum ether to give the title product as a white solid (2.4 g, mp 87.5–88.5° C.).

EXAMPLE 21

Preparation of α,α,α-Trifluoro-2-(isopropylsolfonyl)-2-methyl-p-propionotoluidide

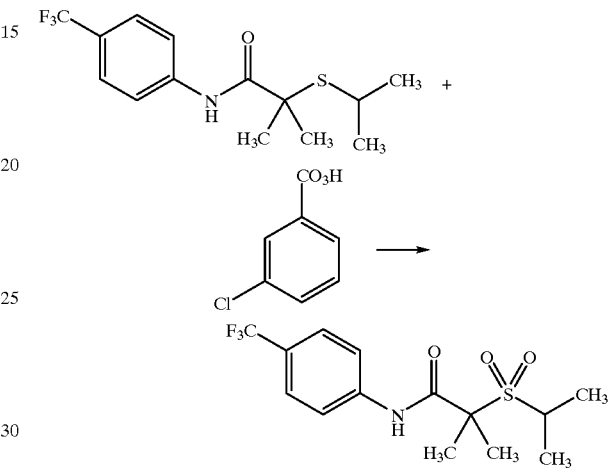

A solution of m-chloroperoxybenzoic acid (3.97 g real, 0.022 mol) in ethyl acetate is added to a solution of α,α,α-trifluoro-2-(isopropylthio)-2-methyl-p-propionotoluidide (3.05 g, 0.01 mol) in ethyl acetate at 5° C. over 45 minutes. After 1 hour, the ice-bath is removed, the reaction mixture is stirred for 2 hours, and diluted with ether. The resultant organic solution is washed sequentially with sodium carbonate solution and water, and concentrated in vacuo to obtain a residue. The residue is crystallized from hexanes to give the title product as yellow needles (2.65 g, mp 101.5–103.0° C.).

EXAMPLE 22

Preparation of 4'-Chloro-3-hydroxy-2,2,4-trimethyl-valeranilide, acetate (ester)

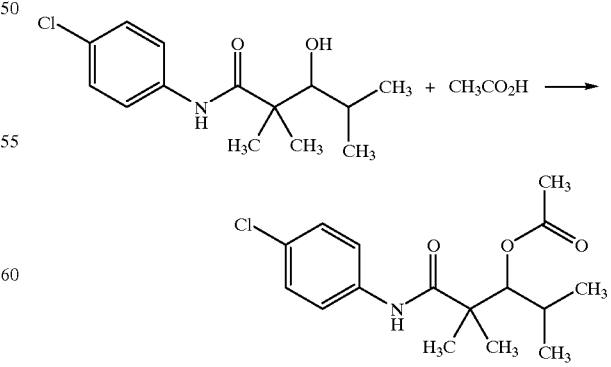

A solution of 4'-chloro-3-hydroxy-2,2,4-trimethyl-valeranilide (2.7 g, 0.01 mol) and acetic acid (0.60 g, 0.01 mol) in methylene chloride containing a few crystals of dimethylaminopyridine is treated with a solution of dicyclohexylcarbodiimide (2.06 g, 0.01 mol) in methylene chloride, stirred at room temperature overnight, and filtered. The resultant filtrate is concentrated in vacuo and the residue is crystallized from a benzene/hexanes solution to obtain a solid. Flash column chromatography of the solid using silica gel and a 3% ethyl acetate in methylene chloride solution gives the title product as a white solid (0.8 g, mp 117.0–118.0° C.).

EXAMPLE 23

Preparation of Ethyl (isopropylthio)acetate

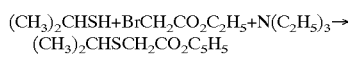

Ethyl bromoacetate (19.5 g, 0.11 mol) is added to a mixture of 2-propanethiol (7.77 g, 0.1 mol) and triethylamine (15.4 mL, 0.11 mol) in methylene chloride. The reaction mixture is stirred at room temperature for 20 hours, diluted with methylene chloride, washed sequentially with water and brine, dried over anhydrous magnesium sulfate, and concentrated in vacuo to obtain the title product as a colorless liquid which is identified by NMR spectral analysis.

EXAMPLE 24

Preparation of Ethyl 2-(isopropylthio)proionate

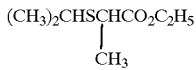

A solution of diisopropylamine (15.4 mL, 0.11 mol) in tetrahydrofuran is cooled to 0° C., treated dropwise with a 2.04 M solution of n-butyllithium in tetrahydro-furan (51.4 mL, 0.105 mol), stirred at 0° C. for 30 minutes, treated dropwise with ethyl (isopropylthio)acetate (16.3 g, 0.1 mol), stirred at 0° C. for 1 hour, treated with methyl iodide (15.6 g, 0.11 mol), stirred at room temperature for 20 hours, and poured into an ice-water mixture (100 g) containing 15 mL of 6 N hydrochloric acid. The resulting aqueous mixture is extracted with ether. The combined organic extracts are washed sequentially with water, saturated sodium thiosulfate solution, water and brine, dried over anhydrous magnesium sulfate, and concentrated in vacuo to obtain a brown solution. Vacuum distillation of the brown solution gives the title product as a liquid (10.0 g) which is identified by NMR spectral analysis.

EXAMPLE 25

Preparation of Ethyl 2-(isopropylthio)-2-methylpropionate

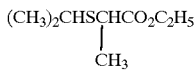

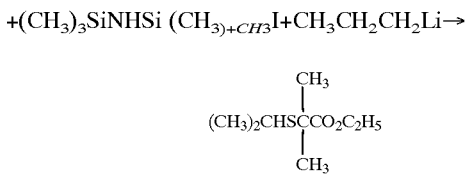

A solution of 1,1,1,3,3,3-hexamethyldisilazane (10.4 mL, 48 mmol) in tetrahydrofuran is cooled to 0° C., treated with a 2.04 M solution of n-butyllithium in tetrahydrofuran (22.6 mL, 46 mmol), stirred at 0° C. for 30 minutes, treated dropwise with ethyl 2-(isopropylthio)propionate (7.6 g, 42 mmol), stirred at 0° C. for 1 hour, treated with methyl iodide, stirred at room temperature for 22 hours, and poured into an ice-water mixture (100 g) containing 10 mL of 6 N hydrochloric acid. The resultant aqueous mixture is extracted with ether. The combined organic extracts are washed sequentially with water and brine, dried over anhydrous magnesium sulfate, and concentrated in vacuo to obtain a brown liquid. Vacuum distillation of the brown liquid gives the title product as a liquid (6.8 g) which is identified by NMR spectral analysis.

EXAMPLE 26

Preparation of 2-(Isopropylthio)-2-methylpropionic acid

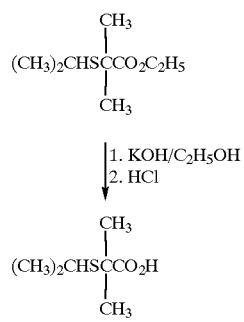

A mixture of ethyl 2-(isopropylthio)-2-methylpropionate (5.4 g, 30 mmol) and potassium hydroxide (5.0 g, 90 mmol) in ethanol is refluxed for 6 hours, cooled, and concentrated in vacuo to obtain a residue. The residue is diluted with water, washed with ether, acidified with hydrochloric acid, and extracted with ether. The combined organic extracts are washed sequentially with water and brine, dried over anhydrous magnesium sulfate, and concentrated in vacuo to obtain a solid. The solid is washed with chloroform and dried under reduced pressure to give the title product as a solid, mp 51.5–52.5° C.

EXAMPLE 27

Preparation of α,α,α-Trifluoro-2-(isopropylthio)-2-methyl-p-propionotoluidide

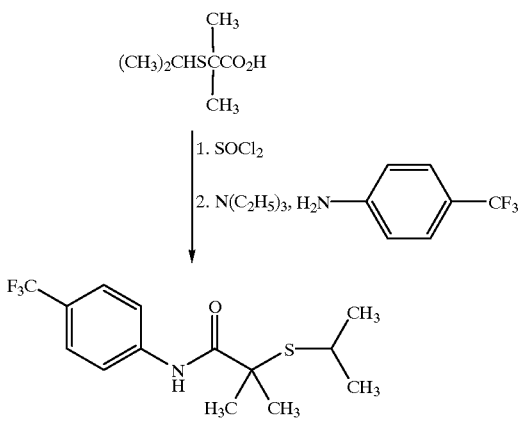

A mixture of 2-(isopropylthio)-2-methylpropionic acid (3.6 g, 22 mmol) and thionyl chloride (2.98 g, 25 mmol) in toluene is heated at 110–125° C. for 6 hours, cooled to 0° C., treated with triethylamine (2.55 g, 25 mmol), stirred at 0° C. for 10 minutes, treated dropwise with p-aminobenzyltrifluoride (3.6 g, 22 mmol), stirred at room temperature for 19 hours, and diluted with ether. The resultant organic solution is washed sequentially with water and brine, dried over anhydrous magnesium sulfate, and concentrated in vacuo to obtain a brown solid. The brown solid is recrystallized from ether to give the title product as tan needles (3.3 g, mp 105–107° C.).

EXAMPLE 28

Evaluation of test compounds against corn rootworms

Test solutions are prepared by dissolving the test compound in a 35% acetone in water mixture to give a concentration of 10,000 ppm. Subsequent dilutions are made with water as needed.

*Diabrotica undecimrunctata* howardi, $3^{rd}$ instar southern corn rootworm

One cc of fine talc is placed in a 30 mL wide-mouth screw-top glass jar. One mL of the appropriate acetone test solution is pipetted onto the talc so as to provide 1.25 mg, 0.25 mg or 0.025 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten $3^{rd}$ instar rootworms are added to each jar and the jars are loosely capped to allow air exchange for the larvae. The treatments are held for 5 days when mortality counts are made. Missing larvae are presumed dead, since they decompose rapidly and can not be found.

*Diabrotica virgifera* virgifera Leconte, $3^{rd}$ instar western corn rootworm

One cc of fine talc is placed in a 30 mL wide-mouth screw-top glass jar. One mL of the appropriate acetone test solution is pipetted onto the talc so as to provide 1.25 mg, 0.25 mg or 0.025 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten $3^{rd}$ instar rootworms are added to each jar and the jars are loosely capped to allow air exchange for the larvae. The treatments are held for 5 days when mortality counts are made. Missing larvae are presumed dead, since they decompose rapidly and can not be found.

The tests are rated according to the scale shown below and the data obtained are shown in Table I.

Compounds employed in the above-described evaluations are given a compound number and identified by name. Data in Table I are reported by compound number.

| Rating Scale | |
|---|---|
| 0 = no effect | 5 = 55–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

A blank space indicates that no evaluatian was conducted.

| Compound Number | |
|---|---|
| 1 | α,α,α-Trifluoro-2,2,4-trimethyl-3-oxo-p-valerotoluidide |
| 2 | 4'-Chloro-N,2,2,4-tetramethyl-3-oxo-valer-anilide |
| 3 | 4'-chloro-3-hydroxy-2,2,4-trimethylvaleranilide |
| 4 | α,α,α-Trifluoro-3-hydroxy-2,2,4-trimethyl-p-valerotoluidide |
| 5 | α,α,α-Trifluoro-2-(isopropylthio)-2-methyl-p-propionotoluidide |
| 6 | α,α,α,α',α',α'-Hexafluoro-N-(2,2,4-trimethyl-3-oxovaleryl)-p-tolu-p-toluidide |
| 7 | 4-Chloro-α,α,α-trifluoro-N-(2,2,4-trimethyl-3 oxovaleryl)-p-benzotoluidide |
| 8 | α,α,α,2,6-Pentafluoro-N-(2,2,4#trimethyl-3 oxovaleryl)-p-benzotoluidide |
| 9 | α,α,α-Trifluoro-3-hydroxy-2,2,4-trimethyl-p-valerotoluidide, acetate (ester) |
| 10 | α,α,α-Trifluoro-2,2,4-trimethyl-3-oxo-p-valerotoluidide, 3-oxime |
| 11 | α,α,α-Trifluoro-2,2,4-trimethyl-3-oxo-4-phenyl-p-valerotoluidide |
| 12 | α,α,α-Trifluoro-2-(isopropylsulfinyl)-2-methyl-p-propionotoluidide |
| 13 | α,α,α-Trifluoro-2-(isopropylsulfonyl)-2-methyl-p-propionotoluidide |
| 14 | 4'-chloro-3-hydroxy-2,2,4-trimethylvaler-anilide, acetate (ester) |
| 15 | N-(Ethoxymethyl)-α,α,α-trifluoro-2,2,4-trimethyl-3-oxo-p-valerotoluidide |
| 16 | α,α,α-Trifluoro-3-methoxy-2,2,4-trimethyl-p-valerotoluidide |
| 17 | 3-(Ethoxymethoxy)-α,α,α-trifluoro-2,2,4-trimethyl-p-valerotoluidide |
| 18 | α,α,α-Trifluoro-3-hydroxy-2,2,4-trimethyl-p-valerotoluidide, methanesulfonate (ester) |
| 19 | α,α,α-Trifluoro-2,2,4-trimethyl-3-(2-propynyl oxy)-p-valerotoluidide |
| 20 | 3-Hydroxy-α,α,α-trifluoro-2,2,4-trimethyl-p-valerotoluidide, chloroacetate (ester) |
| 21 | α,α,α-Trifluoro-2,2,4,4-tetramethyl-3-oxo-p-valerotoluidide |

-continued

| Compound Number | |
|---|---|
| 22 | 3-(Allyloxy)-α,α,α-trifluoro-2,2,4-trimethyl-p-valerotoluidide |
| 23 | α,α,α-Trifluoro-3-(isopropoxy)-2,2,4-trimethyl-p-valerotoluidide |
| 24 | 3-Ethoxy-α,α,α-trifluoro-2,2,4-trimethyl-p-valerotoluidide |
| 25 | α,α,α-Trifluoro-1-isobutyrylcyclopropane-carboxy-p-toluidide |
| 26 | 3-(Cyclopentyloxy)-α,α,α-trifluoro-2,2,4-trimethyl-p-valerotoluidide |
| 27 | α,α,α-Trifluoro-3-(hexyloxy)-2,2,4-trimethyl-p-valerotoluidide |
| 28 | 4'-Chloro-3-methoxy-2,2,4-trimethylvaleranilide |
| 29 | α,α,α-Trifluoro-2,4-dimethyl-3-oxo-p-valerotoluidide |
| 30 | α,α,α-Trifluoro-2-isopropoxy-2-methyl-p-propionotoluidide |
| 31 | 2-Chloro-α,α,α-trifluoro-2,4-dimethyl-p-valerotoluidide |
| 32 | 3-(Difluoromethoxy)-α,α,α-trifluoro-2,4-dimethyl-p-valerotoiuidide |
| 33 | α,α,α-Trifluoro-3-hydroxy-2,2,4-trimethyl-p-valerotoiuidide, formate (ester) |
| 34 | 2-tert-Butoxy-α,α,α-trifluoro-2-methyl-p-propionotoluidide |
| 35 | 2-Ethoxy-α,α,α-trifluoro-2-methyl-p-propionotoluidide |
| 36 | α,α,α-Trifluoro-N,2,2,4-tetramethyl-3-oxo-p-valerotoluidide |
| 37 | 4'-Chloro-2,2,4-trimethyl-3-oxovaleranilide |

TABLE I

Evaluation of Test Compounds

| Compd. Number | Southern Corn Rootworm | | | Western Corn Rootworm | | |
|---|---|---|---|---|---|---|
| | (50 ppm) | (10 ppm) | (1 ppm) | (50 ppm) | (10 ppm) | (1 ppm) |
| 1 | 9.0 | 9.0 | 9.0 | | | |
| 2 | 3.5 | 0.0 | 0.0 | | | |
| 3 | 8.0 | 4.0 | 0.0 | | | |
| 4 | 9.0 | 0.0 | 0.0 | | | |
| 5 | 9.0 | 0.0 | 0.0 | | | |
| 6 | 9.0 | 9.0 | 2.0 | | | |
| 7 | 9.0 | 9.0 | 0.0 | | | |
| 8 | 4.0 | 0.0 | 0.0 | | | |
| 9 | 8.3 | 8.3 | 0.0 | | | |
| 10 | 7.0 | | | | | |
| 11 | 6.0 | | | | | |
| 12 | 9.0 | 9.0 | 8.0 | 9.0 | 0.0 | 0.0 |
| 13 | 9.0 | 9.0 | 3.0 | | | |
| 14 | 9.0 | 9.0 | 9.0 | | | |
| 15 | | | | 9.0 | 9.0 | 8.0 |
| 16 | | | | 9.0 | 9.0 | 0.0 |
| 17 | | | | 9.0 | 9.0 | 1.0 |
| 18 | | | | 9.0 | 3.0 | 0.0 |
| 19 | | | | 9.0 | 9.0 | 0.0 |
| 20 | | | | 9.0 | 5.0 | 0.0 |
| 21 | | | | 9.0 | 9.0 | 0.0 |
| 22 | | | | 9.0 | 9.0 | 0.0 |
| 23 | | | | 9.0 | 9.0 | 0.0 |
| 24 | | | | 9.0 | 9.0 | 0.0 |
| 25 | | | | 7.0 | 0.0 | 0.0 |
| 26 | | | | 8.0 | 0.0 | 0.0 |
| 27 | | | | 9.0 | 0.0 | 0.0 |
| 28 | | | | 9.0 | 5.0 | 0.0 |
| 29 | | | | 8.5 | 0.0 | 0.0 |
| 30 | | | | 9.0 | 9.0 | 0.0 |
| 31 | | | | 4.0 | 0.0 | 0.0 |
| 32 | | | | 4.0 | 4.0 | 0.0 |
| 33 | | | | 9.0 | 5.0 | 0.0 |
| 34 | | | | 9.0 | 9.0 | 2.0 |
| 35 | | | | 9.0 | 3.0 | 0.0 |
| 36 | | | | 9.0 | 9.0 | 2.0 |
| 37 | 9.0 | 9.0 | 0.0 | | | |

What is claimed is:

1. A compound having the structural formula

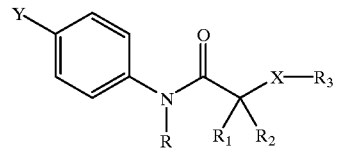

wherein

Y is halogen, $C_1$–$C_4$alkyl, $C_1$–$C_4$haloalkyl, $C_1$–$C_4$alkoxy, $C_1$–$C_4$haloalkoxy, nitro or cyano;

R is hydrogen,
$C_1$–$C_4$alkyl optionally substituted with one $C_1$–$C_4$alkoxy group, or
benzoyl optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;

$R_1$ is $C_1$–$C_4$alkyl and $R_2$ is $C_1$–$C_4$alkyl or halogen, or $R_1$ and $R_2$ may be taken together with the carbon atom to which they are attached to form a cyclopropyl ring;

X is

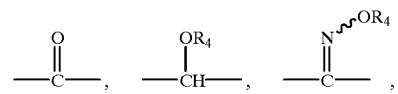

O or $S(O)_n$;

n is an integer of 0, 1 or 2;

$R_3$ is $C_3$–$C_6$cycloalkyl, or
$C_1$–$C_6$alkyl optionally substituted with one phenyl ring wherein the phenyl ring is optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;

R4 is hydrogen, $C_1$–$C_8$alkyl, $C_1$–$C_8$haloalkyl, $C_1$–$C_6$acyl, $C_3$–$C_6$haloacyl, $C_1$–$C_4$alkoxymethyl, $C_3$–$C_6$cycloalkyl, $C_3$–$C_6$alkenyl, $C_3$–$C_6$alkynyl or $S(O)_nR_5$; and $R_5$ is $C_1$–$C_4$alkyl or $C_1$–$C_4$haloalkyl; and the optical isomers, tautomers, agriculturally acceptable salts and agriculturally acceptable metal chelates thereof;

provided that Y cannot be methyl or methoxy when X is

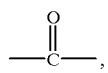

R is hydrogen, $R_1$ and $R_2$ are methyl, and $R_3$ is isopropyl.

2. The compound according to claim 1 wherein

Y is halogen or $C_1$–$C_4$haloalkyl;

$R_1$ and $R_2$ are each independently $C_1$–$C_4$alkyl;

X is

O or $S(O)_n$;

n is an integer of 1 or 2;

$R_3$ is $C_1$–$C_6$alkyl; and $R_4$ is $C_1$–$C_8$alkyl, $C_1$–$C_6$acyl, $C_1$–$C_4$alkoxymethyl, $C_3$–$C_6$alkenyl, or $C_3$–$C_6$alkynyl.

3. The compound according to claim 2 wherein

Y is Cl or trifluoromethyl;

R is hydrogen, $C_1$–$C_4$alkyl, $C_1$–$C_4$alkoxymethyl, or benzoyl optionally substituted with one or more groups in dependently selected from halogen, $C_1$–$C_4$alkyl, $C_1$–$C_4$haloalkyl, $C_1$–$C_4$alkoxy or $C_1$–$C_4$haloalkoxy groups;

$R_1$ and $R_2$ are methyl;

$R_3$ is isopropyl or tert-butyl; and $R_4$ is $C_1$–$C_4$alkyl, $C_2$–$C_6$acyl, $C_1$–$C_4$alkoxymethyl, allyl or propargyl.

4. The compound according to claim 3 wherein

R is hydrogen, $C_1$–$C_4$alkyl or $C_1$–$C_4$alkoxymethyl;

X is

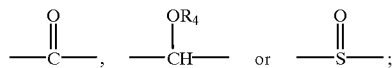

$R_3$ is isopropyl; and $R_4$ is $C_2$–$C_6$acyl.

5. The compound according to claim 4 selected from the group consisting of

α,α,α-trifluoro-2,2,4-trimethyl-3-oxo-p-valerotoluidide;

α,α,α-trifluoro-2-(isopropylsulfinyl)-2-methyl-p-propionotoluidide;

4'-chloro-3-hydroxy-2,2,4-trimethylvaleranilide, acetate (ester);

α,α,α-trifluoro-N,2,2,4-tetramethyl-3-oxo-p-valerotoluidide; and

N-(ethoxymethyl)-α,α,α-trifluoro-2,2,4-trimethyl-3-oxo-p-valerotoluidide.

6. A method for the control of insect pests which comprises contacting said pests, or their food supply, habitat or breeding grounds with a pesticidally effective amount of a compound having the structural formula

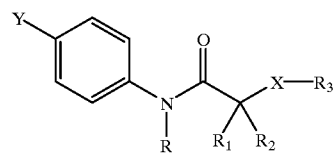

wherein

Y is halogen, $C_1$–$C_4$alkyl, $C_1$–$C_4$haloalkyl, $C_1$–$C_4$alkoxy, $C_1$–$C_4$haloalkoxy, nitro or cyano;

R is hydrogen,
$C_1$–$C_4$alkyl optionally substituted with one $C_1$–$C_4$alkoxy group, or
benzoyl optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;

$R_1$ is $C_1$–$C_4$alkyl and $R_2$ is $C_1$–$C_4$alkyl or halogen, or $R_1$ and $R_2$ may be taken together with the carbon atom to which they are attached to form a cyclopropyl ring;

X is

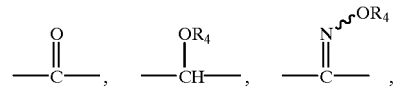

O or $S(O)_n$;

n is an integer of 0, 1 or 2;

$R_3$ is $C_3$–$C_6$cycloalkyl, or
$C_1$–$C_6$alkyl optionally substituted with one phenyl ring wherein the phenyl ring is optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;

R4 is hydrogen, $C_1$–$C_8$alkyl, $C_1$–$C_8$haloalkyl, $C_1$–$C_6$acyl, $C_1$–$C_6$haloacyl, $C_1$–$C_4$alkoxymethyl, $C_3$–$C_6$cycloalkyl, $C_3$–$C_6$alkenyl, $C_3$–$C_6$alkynyl or $S(O)_nR_5$; and $R_5$ is $C_1$–$C_4$alkyl or $C_1$–$C_4$haloalkyl; and the optical isomers, tautomers, agriculturally acceptable salts and agriculturally acceptable metal chelates thereof.

7. The method according to claim 6 wherein

Y is halogen or $C_1$–$C_4$haloalkyl;

$R_1$ and $R_2$ are each independently $C_1$–$C_4$alkyl;

X is

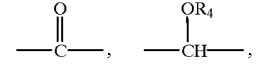

n is an integer of 1 or 2;

$R_3$ is $C_1$–$C_6$alkyl; and $R_4$ is $C_1$–$C_8$alkyl, $C_1$–$C_6$acyl, $C_1$–$C_4$alkoxymethyl, $C_3$–$C_6$alkenyl or $C_3$–$C_6$alkynyl.

8. The method according to claim 7 wherein

Y is Cl or trifluoromethyl;

R is hydrogen, $C_1$–$C_4$alkyl, $C_1$–$C_4$alkoxymethyl, or benzoyl optionally substituted with one or more groups independently selected from halogen, $C_1$–$C_4$alkyl, $C_1$–$C_4$haloalkyl, $C_1$–$C_4$alkoxy or $C_1$–$C_4$haloalkoxy groups;

$R_1$ and $R_2$ are methyl;

$R_3$ is isopropyl or tert-butyl; and $R_4$ is $C_1$–$C_4$alkyl, $C_2$–$C_6$acyl, $C_1$–$C_4$alkoxymethyl, allyl or propargyl.

9. The method according to claim 8 wherein

R is hydrogen, $C_1$–$C_4$alkyl or $C_1$–$C_4$alkoxymethyl;

X is

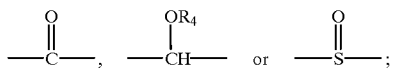

$R_3$ is isopropyl; and $R_4$ is $C_2$–$C_6$acyl.

10. The method according to claim 9 wherein the compound is selected from the group consisting of α,α,α-trifluoro-2,2,4-trimethyl-3-oxo-p-valerotoluidide; α,α,α-trifluoro-2-(isopropylsulfinyl)-2-methyl-p-propionotoluidide;

4'-chloro-3-hydroxy-2,2,4-trimethylvaleranilide, acetate (ester);

α,α,α-trifluoro-N,2,2,4-tetramethyl-3-oxo-p-valerotoluidide; and

N-(ethoxymethyl) -α,α,α-trifluoro-2,2,4-trimethyl-3-oxo-p-valerotoluidide.

11. The method according to claim 6 wherein the insect pests are soil-dwelling Coleoptera.

12. The method according to claim 11 wherein the soil-dwelling Coleoptera is selected from the group consisting of southern corn rootworm, western corn rootworm and Mexican corn rootworm.

13. The method according to claim 11 wherein the compound is applied to the soil in which the Coleoptera are dwelling.

14. The method according to claim 13 wherein the compound is applied to the soil at a rate of about 0.1 kg/ha to 10 kg/ha.

15. A method for the protection of growing plants from attack or infestation by insect pests which comprises applying to the foliage of the plants, or to the soil or water in which they are growing or are to be grown, a pesticidally effective amount of a compound having the structural formula

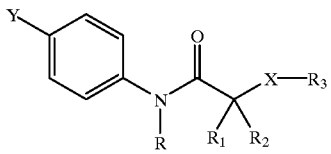

wherein

Y is halogen, $C_1$–$C_4$alkyl, $C_1$–$C_4$haloalkyl, $C_1$–$C_4$alkoxy, $C_1$–$C_4$haloalkoxy, nitro or cyano;

R is hydrogen, $C_1$–$C_4$alkyl optionally substituted with one $C_1$–$C_4$alkoxy group, or benzoyl optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;

$R_1$ is $C_1$–$C_4$alkyl and $R_2$ is $C_1$–$C_4$alkyl or halogen, or $R_1$ and $R_2$ may be taken together with the carbon atom to which they are attached to form a cyclopropyl ring;

X is

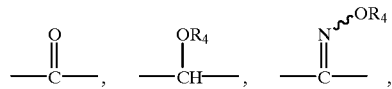

O or $S(O)_n$;

n is an integer of 0, 1 or 2;

$R_3$ is $C_3$–$C_6$cycloalkyl, or $C_1$–$C_6$alkyl optionally substituted with one phenyl ring wherein the phenyl ring is optionally substituted with one or more groups independently selected from halogen, $C_1$–$C_4$alkyl, $C_1$–$C_4$haloalkyl, $C_1$–$C_4$alkoxy, $C_1$–$C_4$haloalkoxy, nitro and cyano groups;

$R_4$ is hydrogen, $C_1$–$C_8$alkyl, $C_1$–$C_8$haloalkyl, $C_1$–$C_6$acyl, $C_1$–$C_6$haloacyl, $C_1$–$C_4$alkoxymethyl, $C_3$–$C_6$cycoalkyl, $C_3$–$C_6$alkenyl, $C_3$–$C_6$alkynyl or $S(O)_nR_5$; and $R_5$ is $C_1$–$C_4$alkyl or $C_1$–$C_4$haloalkyl; and the optical isomers, tautomers, agriculturally acceptable salts and agriculturally acceptable metal chelates thereof.

16. The method according to claim 15 wherein

Y is halogen or $C_1$–$C_4$haloalkyl;

$R_1$ and $R_2$ are each independently $C_1$–$C_4$alkyl;

X is

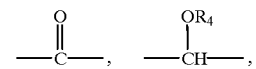

O or $S(O)_n$;

n is an integer of 1 or 2;

$R_3$ is $C_1$–$C_6$alkyl; and $R_4$ is $C_1$–$C_8$alkyl, $C_1$–$C_6$acyl, $C_1$–$C_4$alkoxymethyl, $C_3$–$C_6$alkenyl or $C_3$–$C_6$alkynyl.

17. The method according to claim 16 wherein

Y is Cl or trifluoromethyl;

R is hydrogen, $C_1$–$C_4$alkyl, $C_1$l–$C_4$alkoxymethyl, or benzoyl optionally substituted with one or more groups independently selected from halogen, $C_1$–$C_4$alkyl, $C_1$–$C_4$haloalkyl, $C_1$–$C_4$alkoxy or $C_1$–$C_4$haloalkoxy groups;

$R_1$ and $R_2$ are methyl;

$R_3$ is isopropyl or tert-butyl; and $R_4$ is $C_1$–$C_4$alkyl, $C_2$–$C_6$acyl, $C_1$–$C_4$alkoxymethyl, allyl or propargyl.

18. The method according to claim 17 wherein

R is hydrogen, $C_1$–$C_4$alkyl or $C_1$–$C_4$alkoxymethyl;

X is

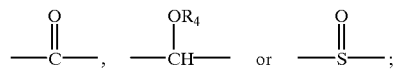

$R_3$ is isopropyl; and $R_4$ is $C_2$–$C_6$acyl.

19. The method according to claim 18 wherein the compound is selected from the group consisting of α,α,α-trifluoro-2,2,4-trimethyl-3-oxo-p-valerotoluidide;

α,α,α-trifluoro-2-(isopropylsulfinyl)-2-methyl-p-propionotoluidide;

4'-chloro-3-hydroxy-2,2,4-trimethylvaleranilide, acetate (ester);

α,α,α-trifluoro-N,2,2,4-tetramethyl-3-oxo-p-valerotoluidide; and

N-(ethoxymethyl)-α,α,α-trifluoro-2,2,4-trimethyl-3-oxo-p-valerotoluidide.

20. The method according to claim 15 wherein the insect pests are soil-dwelling Coleoptera.

21. The method according to claim 20 wherein the soil-dwelling Coleoptera is selected from the group consisting of southern corn rootworm, western corn rootworm and Mexican corn rootworm.

22. The method according to claim 15 wherein the plant is selected from the group consisting of corn, potato, sugar beets, wheat, peanuts, a turfgrass and soybeans.

23. The method according to claim 22 wherein the plant is corn.

24. The method according to claim 15 wherein the compound is applied to the soil in which the plants are growing or are to be grown.

25. The method according to claim 15 wherein the compound is applied to the plants or to the soil in which they are growing or are to be grown at a rate of about 0.1 kg/ha to 10 kg/ha.

* * * * *